United States Patent
Rehner et al.

(10) Patent No.: US 11,480,637 B2
(45) Date of Patent: Oct. 25, 2022

(54) LOCAL COIL WITH SEGMENTED ANTENNA DEVICE

(71) Applicant: Siemens Healthcare GmbH, Erlangen (DE)

(72) Inventors: Robert Rehner, Neunkirchen am Brand (DE); Stephan Zink, Nuremberg (DE); Thomas Kundner, Buckenhof (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/914,627

(22) Filed: Jun. 29, 2020

(65) Prior Publication Data

US 2021/0003645 A1 Jan. 7, 2021

(30) Foreign Application Priority Data

Jul. 4, 2019 (EP) .................................... 19184394

(51) Int. Cl.
*G01R 33/34* (2006.01)
*A61B 5/055* (2006.01)

(52) U.S. Cl.
CPC ........ *G01R 33/34084* (2013.01); *A61B 5/055* (2013.01); *G01R 33/34007* (2013.01)

(58) Field of Classification Search
CPC ........ G01R 33/34084; G01R 33/34007; A61B 5/055
See application file for complete search history.

(56) References Cited

U.S. PATENT DOCUMENTS

| | | | |
|---|---|---|---|
| 5,168,230 A | 12/1992 | Hashoian | |
| 2007/0262777 A1 | 11/2007 | Warntjes | |
| 2008/0129296 A1 | 6/2008 | Fischer | |
| 2008/0284435 A1 | 11/2008 | Overweg | |
| 2011/0166437 A1* | 7/2011 | Chang | A61B 5/055 600/411 |
| 2012/0182015 A1* | 7/2012 | Driemel | G01R 33/3685 324/322 |
| 2013/0021035 A1 | 1/2013 | Kundner | |
| 2013/0137969 A1* | 5/2013 | Jones | A61B 5/055 600/421 |
| 2014/0210466 A1* | 7/2014 | Arias | G01R 33/34084 324/309 |
| 2015/0323624 A1* | 11/2015 | Feinberg | G01R 33/34007 324/309 |

(Continued)

FOREIGN PATENT DOCUMENTS

| | | |
|---|---|---|
| DE | 102006055136 A1 | 5/2008 |
| DE | 102011079564 A1 | 1/2013 |

(Continued)

OTHER PUBLICATIONS

European Search Report for European Application No. 19184394.5-1010 dated Jan. 15, 2020.

*Primary Examiner* — G. M. A Hyder
(74) *Attorney, Agent, or Firm* — Lempia Summerfield Katz LLC (57) ABSTRACT

A local coil for a magnetic resonance tomography scanner has an antenna. The antenna has a conductor loop and a plurality of electronic function groups, which are arranged in a distributed manner spaced apart from one another along the conductor loop and are electrically connected to one another by flexible conductor segments.

16 Claims, 4 Drawing Sheets

(56) References Cited

U.S. PATENT DOCUMENTS

2019/0154774 A1* 5/2019 Hushek ............ G01R 33/34007
2019/0227133 A1 7/2019 Leussler
2020/0081082 A1 3/2020 Kundner

FOREIGN PATENT DOCUMENTS

| DE | 102018215457 A1 | 3/2020 |
| WO | WO2005052621 A1 | 6/2005 |
| WO | WO2018069247 A1 | 4/2018 |

* cited by examiner

LOCAL COIL WITH SEGMENTED ANTENNA DEVICE

RELATED CASE

This application claims the benefit of European Application EP19184394.5, filed on Jul. 4, 2019, which is hereby incorporated by reference in its entirety.

FIELD

The present embodiments relate to a local coil for a magnetic resonance tomography scanner with an antenna device, wherein the antenna device has a conductor loop and a plurality of electronic function groups.

BACKGROUND

Magnetic resonance tomography scanners are imaging devices that, in order to image an examination object, align nuclear spins of the examination object by a strong external magnetic field and excite them by a magnetic alternating field for precession around said alignment. The precession or return of the spins from this excited state into a state with less energy in turn generates, as a response, a magnetic alternating field, which is received by way of antennas.

With the aid of magnetic gradient fields, a spatial encoding is impressed onto the signals. The spatial encoding permits an assignment of the received signal to a volume element. The received signal is then evaluated, and a three-dimensional imaging representation of the examination object is provided.

To achieve the best possible signal-to-noise ratio (SNR), the antenna coils for the reception are arranged as close to the patient as possible. This is done using so-called local coils, which are normally connected to the magnetic resonance tomography scanner using cable connections. To simplify the use and to reduce the number of different variants, there are local coil arrays or matrices which can be used for different purposes. However, rigid cable connections and bulky electronic elements in these local coil arrays are inconvenient.

SUMMARY AND DETAILED DESCRIPTION

The object is to improve local coils for versatile use.

The local coil for a magnetic resonance tomography scanner has an antenna device with a conductor loop and a plurality of electronic function groups. An electrical device that is designed to receive electrical and/or magnetic alternating fields in a predetermined frequency range from a spatial volume adjacent the local coil and to pass them as electrical or optical signals via a signal connection or a wireless connection to the magnetic resonance tomography scanner for imaging purposes is here regarded as an antenna device. The alternating fields are preferably magnetic resonance signals from excited nuclear spins from a patient with a frequency termed a Larmor frequency, said magnetic resonance signals being determined by the type of the nuclear spins and a static magnetic field BO of the magnetic resonance tomography scanner. The conductor loop is here designed as an induction loop.

The electronic function groups of the local coil are arranged in a distributed manner spaced apart from one another. It is conceivable here for the function groups to be arranged along the extent of the conductor loop. The electronic function groups can however also be arranged on or between flexible conductor segments that connect individual conductor loops to an antenna matrix or an antenna array. Preamplifiers (LNA, low noise amplifier), baluns (balancer/unbalancer), mixers, diplexers, impedance matching networks, active and passive detuning and tuning circuits and safety circuits for protection of the antenna and/or patient are in particular regarded as electronic function groups here. All components that have to work together to satisfy a single one of these functions and are therefore also arranged as a group spatially adjacent to one another are in each case regarded as an electronic function group.

The electronic function groups are here electrically connected to one another by flexible conductor segments. Flexible conductor segments are here electrical conductors that form subsections of the conductor loop and adapt themselves to the shape of the patient using small force effects, for example using the net weight of the electronic function groups. It is also conceivable for the local coil to be brought into a desired shape by an operator using manual force. To this end, the local coil can for example also have a shell made of a flexible material or can be divided into multiple connected segments that can be pivoted relative to one another.

In principle, it is also conceivable for the conductor loop to be formed from a single flexible conductor segment if the electronic function groups are themselves formed by components on the flexible conductor segment or are arranged as a separate circuit board, such that unpopulated regions of the flexible conductor segment ensure sufficient movability between the function groups.

Advantageously, a local coil can be provided, thanks to the combination of electronic function groups distributed over the local coil and the flexible connection thereof, which provides a more even thickness and flexibility at the same time as preventing concentrated heat sources caused by central electronics.

In one conceivable embodiment of the local coil, the flexible conductor segments have a flexible circuit board with at least three layers. Conventional flexible circuit boards consist of an insulating carrier material with conductor surfaces, also termed layers, that are arranged on opposing surfaces of the carrier material. In contrast, the flexible conductor segments according to the embodiment have at least one further layer of a conductor and an insulating intermediate layer, such that additional control and signal connections between the electronic function groups can be provided. It is also conceivable that capacitances, for example for capacitive coil enlargement, can be provided by the additional conductor and insulator surfaces. The flexible conductor segments can here be designed as mechanically separate, such that they are mechanically connected to one another only by the electronic function groups, or are only electrically insulated, such that just one or multiple electrical connections between the flexible conductor segments are established, only by the electronic function group.

A flexible circuit board with at least three layers advantageously enables control and signal lines to be realized without separate, freely wired lines. By the conductor surfaces, capacitances provided in multilayer technology thereby advantageously avoid discrete capacitances, the mechanical properties of which are particularly fault-prone on flexible carrier materials during processing.

In one possible embodiment of the local coil, at least one flexible conductor segment and one electronic function group have a form-fit or force-fit, electrically conductive connection and are connected by these electrically and mechanically to one another. The electronic function group can here be arranged on its own circuit board separate from the flexible conductor segment. The electrically conductive connection can for example be a plug-in connection, a clamp connection, or a crimp connection. It is conceivable here for the electronic function group to have two such connections and for two mechanically separate flexible conductor elements to be connected electrically and mechanically to one another via the plug connector and the electrical function group. However, it is also possible for an electronic function group to be fixed to a flexible conductor segment by such a connection and to be electrically connected thereto. The electronic function group can thus establish electrical connections and functions between conductor paths of adjacent flexible conductor segments.

Advantageously, such force-fit and/or form-fit connections enable a low-cost and reliable connection between a flexible conductor segment and an electronic function group. Soldered connections between rigid and flexible elements can in particular be avoided in this way.

However, it is also conceivable in one embodiment of the local coil for components of an electronic function group to be arranged directly on a flexible conductor segment. "Directly" here means that the components are not first arranged on a circuit board and then connected with it to the flexible conductor segment. The electronic components can here for example be soldered to the flexible conductor segment. The flexible conductor segment can in particular in one embodiment with more than two conductor levels also provide conductor paths and/or conductive through-connectors for connection or routing of components of the electronic function group.

In particular, in the case of simple electronic function groups containing small, robust components, the arrangement of the components directly on the flexible conductor segment permits a space-saving design. For example, detune circuits containing few components are distributed over the conductor loop at particular positions in order to achieve optimum effect. This type of arrangement is particularly suitable for regions in which the flexible conductor segment is subject to low mechanical stresses and/or deformations. It is also conceivable for individual sensitive components to be protected against mechanical stresses by separate frames or housings.

In contrast, for mechanically sensitive components and sections of the flexible conductor segments that are subject to greater stress and movements, it may be advantageous to arrange an electronic function group in this section at each required position and to relocate the component to the electronic function group. In a preferred embodiment of the local coil, the flexible conductor segment is braced in the region of the electronic function group. The bracing can be implemented by providing a stiffer carrier material in the flexible conductor segment at the location of the function group, providing additional layers of the carrier material, and/or embodying a layer of the carrier material as thicker than in the adjacent flexible region.

This is conceivable, for example, for extension capacitors or detuning diodes. In this case, the circuit needed to activate the detuning diode can then, for example, also be arranged on the electronic function group in order in this way to achieve a sensible distribution of the rigid, heavy and/or waste-heat-generating elements. However, more complex functions can also be implemented by direct population on a braced region of a flexible conductor segment.

In one possible embodiment of the local coil, a flexible conductor segment has a shielded electrical signal line and/or a control line for the electronic function groups. A signal line in a multilayer flexible circuit board in which the shielding effect is achieved, comparably to a coaxial shielding around a central core of a conventional coaxial cable, by conductor surfaces adjacent to a signal line in a flexible circuit board in the multilayer circuit board is regarded as a shielded signal line. Preferably, in this case, the adjacent conductor surfaces are in signal connection with a ground potential of the signals. The signal line can here be provided, comparably to a coaxial line, with an asymmetrical core or differentially by two symmetrical signal cores. A control line is here a signal line designed to transmit a signal for the function of an electrical function group that is not a magnetic resonance signal. Preferably, these are auxiliary or control signals that are transmitted from the magnetic resonance tomography scanner to the local coil, such as for example, detuning, clock pulse or auxiliary frequency signals and supply voltages. Because of higher signal levels or other irradiation resistance, a shielding by adjacent conductor surfaces can also be omitted here.

The mechanical structure of the antenna device can advantageously be simplified by additional signal lines in the flexible conductor segment.

In one conceivable embodiment of the local coil, a flexible conductor segment has a standing wave trap. Standing wave traps can be necessary in particular in flexible conductor segments between individual conductor loops of an antenna matrix with larger dimensions, in order to prevent the circuit being overloaded or patients being put at risk by induced currents and voltages. A filter that prevents the propagation of an electrical signal with the Larmor frequency over one or more conductors of the flexible conductor segment is in particular regarded as a standing wave trap. Such a signal is for example induced if the magnetic resonance tomography scanner transmits a radio frequency signal with the Larmor frequency to excite the nuclear spins to be examined. In a preferred embodiment, the flexible conductor segment is here rolled up as part of the standing wave trap to form a drum or coil.

An inductance for a standing wave trap can advantageously be provided by rolling up the flexible conductor segment to form a drum or coil without additional conductors or connection points.

In one possible embodiment of the local coil, the local coil has a plurality of antenna devices with a plurality of antenna loops. The antenna devices can here be all identical or else be associated with different, previously described embodiments. The antenna devices here preferably form a matrix, in which the surfaces enclosed by the conductor loops only partially overlap and in each case individually at least partially overlap disjunct surfaces, in order to receive magnetic resonance signals from different regions of the examination object. The plurality of antenna devices here has plug-in connections on the conductor loops, with which the antenna devices are connected electrically and also mechanically to one another. It is conceivable for an antenna matrix of the local coil to be formed in this way from identical antenna devices. The plug-in connection can here, for example, exchange induced magnetic resonance signals between the conductor loops, in order to provide a decoupling of the conductor loops. It is however also conceivable for control signals, clock pulses, oscillator signals or also supply voltages and currents to be distributed in this way across the antenna devices of the local coil by flexible conductor segments without additional free wiring.

A low-cost provision of an antenna matrix of the local coil is advantageously possible via the plug-in connections between the conductor loops.

The present invention is defined by the following claims, and nothing in this section should be taken as a limitation on those claims. Any teaching for one type of claim (e.g., method) may be applicable to another type of claim (e.g., computer readable storage medium or system). Further aspects and advantages of the invention are discussed below in conjunction with the preferred embodiments and may be later claimed independently or in combination.

BRIEF DESCRIPTION OF THE DRAWINGS

The above-described characteristics, features and advantages of this invention, as well as the manner in which these are achieved, will become clearer and more readily understandable in connection with the following description of the exemplary embodiments, which are explained in more detail in conjunction with the drawings, in which drawings.

DETAILED DESCRIPTION OF THE PREFERRED EMBODIMENTS

Figure 1:
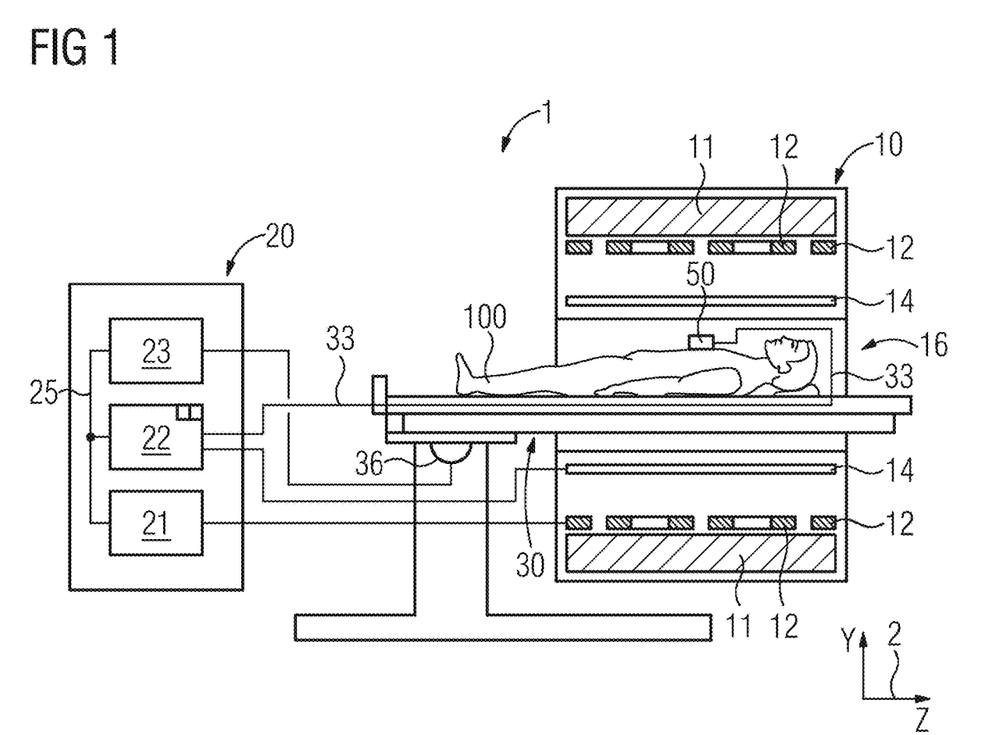
FIG. 1 shows a schematic overview representation of a magnetic resonance tomography scanner with one embodiment of a local coil.

FIG. 1 shows a schematic representation of an embodiment of a magnetic resonance tomography scanner 1 having an inventive local coil 50.

The magnet unit 10 has a field magnet 11, which generates a static magnetic field BO for aligning nuclear spins of samples or of the patient 100 in an acquisition zone. The acquisition zone is characterized by an extremely homogeneous static magnetic field BO, the homogeneity relating in particular to the magnetic field strength or the absolute value. The acquisition zone is virtually spherical in shape and is arranged in a patient tunnel 16, which extends in a longitudinal direction 2 through the magnet unit 10. A patient couch 30 is movable in the patient tunnel 16 by the positioning unit 36. Typically, the field magnet 11 is a superconducting magnet, which is able to provide magnetic fields having a magnetic flux density of up to 3T, even more in more recent devices. For lower field strengths, however, permanent magnets or electromagnets having normal-conducting coils can also be used.

The magnet unit 10 further includes gradient coils 12, which are configured, for spatial differentiation of the captured imaging regions in the examination volume, to overlay variable magnetic fields onto the magnetic field BO in three spatial directions. The gradient coils 12 are typically coils made of normally conducting wires, which can generate mutually orthogonal fields in the examination volume.

The magnet unit 10 also includes a body coil 14, which is configured to radiate a radio frequency signal supplied by way of a signal line into the examination volume and to receive resonance signals emitted by the patient 100 and output said signals by way of a signal line. However, the magnetic resonance signal from the patient is preferably acquired by the local coil 50 explained in greater detail below, which is arranged closer to the patient 100.

A control unit or controller 20 supplies the magnet unit 10 with the different signals for the gradient coils 12 and the body coil 14 and evaluates the received signals.

Thus, the control unit 20 has a gradient control 21 which is designed to provide the gradient coils 12 with variable currents by way of supply lines, which variable currents provide the desired gradient fields in the examination volume on a temporally coordinated basis.

Furthermore, the control unit 20 includes a radio frequency unit or generator 22, which is designed to generate a radio frequency pulse with a predetermined temporal sequence, a predetermined amplitude and spectral power distribution for excitation of a magnetic resonance of the nuclear spins in the patient 100. Pulse powers in the kilowatt range can be achieved in this case. The excitation pulses can be radiated into the patient 100 by way of the body coil 14 or also by way of a local transmit antenna.

A controller 23 communicates with the gradient controller 21 and the radio frequency unit 22 via a signal bus 25.

The local coil 50 is arranged on the patient 100 and is in wired or wireless signal connection with the radio frequency unit 22.

Figure 2:
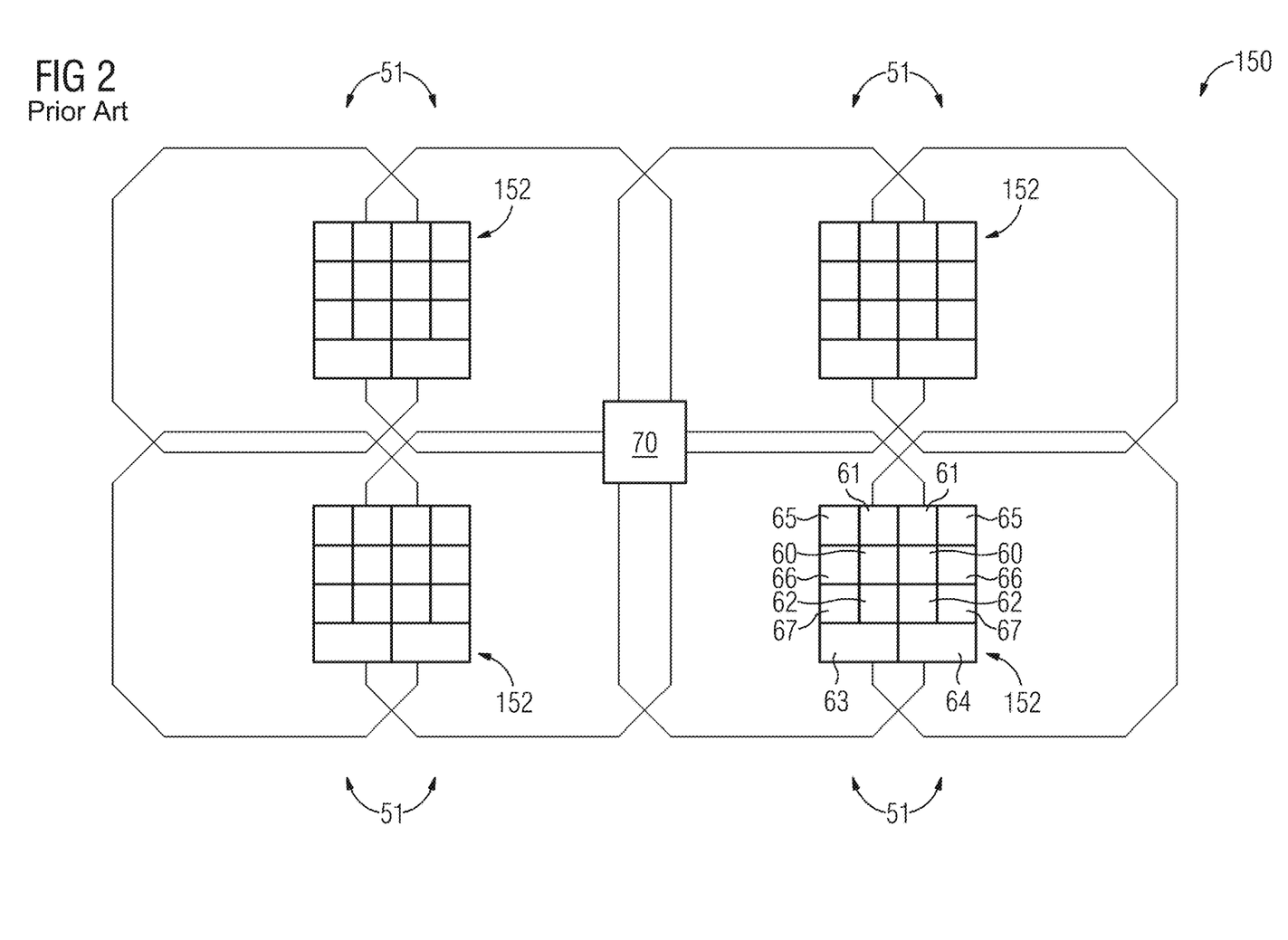
FIG. 2 shows a schematic representation of a local coil according to the prior art.

FIG. 2 shows a schematic representation of a conventional local coil 150 according to the prior art. The conventional local coil 150 has a plurality of conductor loops 51, which form an antenna matrix or array. The conductor loops 51 partially overlap, in order to induce a decoupling between adjacent conductor loops 51 due to the opposite flux direction of the magnetic field in overlapping and non-overlapping regions.

In the case of the conventional local coil 150, a central electronics module 152, on which different function groups are combined, is in each case embodied between two conductor loops 51. These are for example a balun 60 and matching network 65, with which the impedance and symmetry of the conductor loop 51 are matched to the first preamplifier level 61. Furthermore, second preamplifier levels or preamplifiers 62 for further amplification, mixers 63 for converting the amplified magnetic resonance signals to an intermediate frequency, and diplexers for combining or separating signals of different frequency, such as oscillator signals, intermediate frequencies and detuning signals for example, are located on the central electronics modules 152.

The signals of the central electronics module 152 are combined via separate signal lines to form a central connection unit 70, to which a cable is directly attached or can be connected via a plug at a corresponding multi-pin jack on the connection unit 70.

Figure 3:
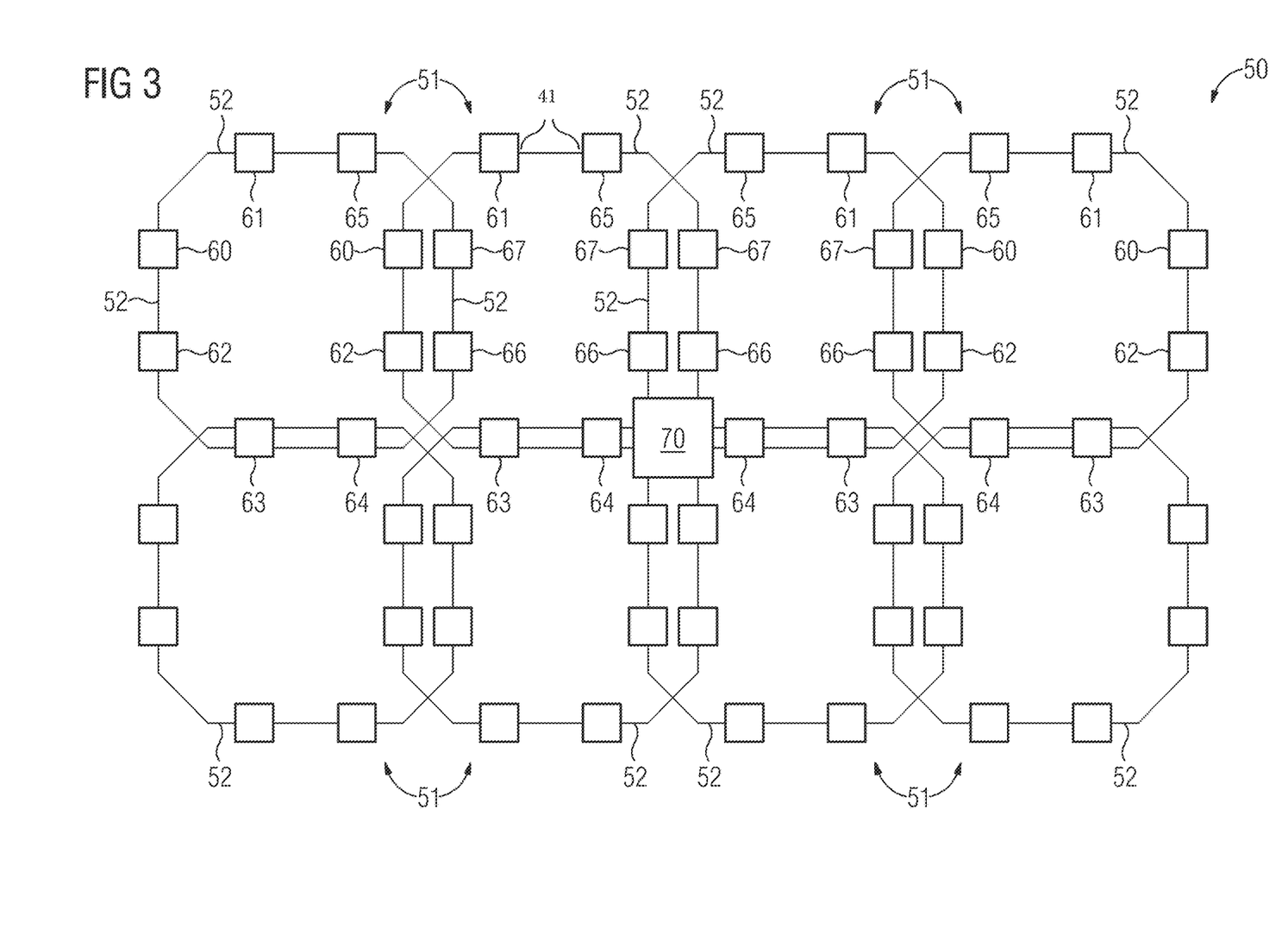
FIG. 3 shows a schematic representation of an embodiment of a local coil with an exemplary distribution of function groups.

FIG. 3 by comparison shows one embodiment of a local coil 50 with an exemplary distribution of function groups. The function groups are here connected by flexible conductor segments 52 to form conductor loops 51.

Thus, for example, function groups such as the balun 60, the first preamplifier 61, and the matching network 65 are connected to one another by flexible conductor segments 52, but at the same time are arranged spaced apart from one another along the conductor loop 51. Since the balun 60 and the matching network 65 ensure an electrical matching of the signals of the conductor loop 51 to the first preamplifier level 61, it is advantageous to arrange these in each case adjacent to one another along the extent of the conductor loop 51. The same applies for the second amplifier level 62, which forwards its output signal via the mixer 63 and the diplexer 64. These too are hence preferably arranged adjacent to one another along the conductor loop 51.

Indirect parts of the closed conductor loop here, in the sense that they are also electrically incorporated into the conductor loop 51, are the function units such as fuse 67, detuning circuit 66, matching network 65, or first preamplification level 61, which directly process or influence the MR signal received from the conductor loop 51 as an antenna coil.

Since in addition the mixer 63 and the diplexer 64 combine and forward the signals of two conductor loops 51, the mixer 63 and the diplexer 64 are preferably arranged in a region in which two conductor loops 51 overlap, the signals of which are then combined.

The conductor loops 51 are arranged at or on a flexible carrier material 81, as explained in greater detail below in respect of FIG. 4. Further function units, such as the aforementioned mixer 63, diplexer 64 or second amplification levels 62 and balun 60, are arranged along the conductor loop 51, but are not incorporated directly into this electrically, and on the shared flexible carrier material 81. These are connected by separate conductors on the flexible carrier material 81 as supply, signal or control lines to the other units and/or the connection unit 70.

Preferably, one or more electronic function groups are here formed directly on the flexible conductor segment 52, in that the flexible conductor segment provides the connection and supply lines and the components are populated directly on the flexible conductor segment 52. To relieve the mechanical stress on the components of the electronic function group, additional layers of the flexible carrier material 81 are then preferably provided in the region populated with the components. The flexible carrier material 81 is embodied as thicker in this region in one or more layers and/or layers are embodied with a stiffer carrier material, such that the flexible conductor segment 52 is braced in the region of the electronic function group and mechanical forces on the components and the soldered connections are significantly reduced. The function module can in this way advantageously be embodied as integral with the flexible conductor segment and fault-prone connections are avoided.

The function groups can however also be embodied as single- or multi-layered separate circuit boards. The circuit boards can be embodied as rigid, in order to protect sensitive components such as ceramic capacitors, which are attached or soldered thereto, against mechanical stress. The individual circuit boards are then preferably embodied as small in their extension parallel to the conductor loop 51, for example smaller than half, a third or a quarter of an extension of a connecting flexible conductor segment 52. Thus the entire conductor loop 51 as a composite of flexible and rigid elements nevertheless has sufficient flexibility. In principle, it is however conceivable for the circuit board of a function group also to be designed flexibly for less sensitive components.

A connection between function group and a flexible conductor segment 52 is effected preferably for separate circuit boards by a form-fit and/or force-fit, electrically conductive connection 41. For example, the circuit boards of the function group can be connected to one another by a complementary plug/jack system. A clamping device is also conceivable, by which the flexible conductor segment 52 is electrically and mechanically connected.

Figure 4:
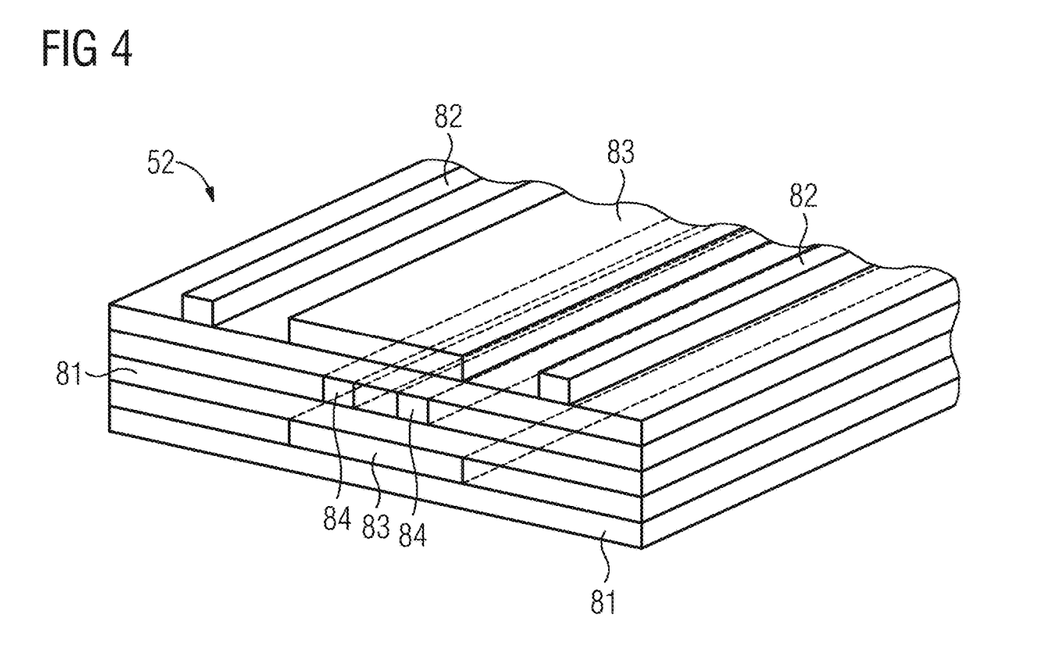
FIG. 4 shows a schematic representation of an embodiment of a flexible conductor segment.

FIG. 4 schematically represents a flexible conductor segment 52. The flexible conductor segment 52 has multiple layers of a flexible insulator as a flexible carrier material 81. This flexible carrier material 81 is preferably a dielectric featuring high quality and low dielectric losses. Layers of a conductor material are arranged between or also on these flexible carrier materials 81. The carrier material is, for example, embodied as foils or wires made of material with good conductivity or metal such as copper, silver or aluminum. These can be embodied flat as shielding areas 83 or also as conductor paths 82, 84. Conductor paths 82 that are not surrounded by shielding areas 83 can, for example, be embodied as a conductor loop 51 for receiving magnetic resonance signals. In contrast, conductor paths 84 that are arranged between two shielding areas 83 can be provided for forwarding magnetic resonance signals and/or control signals. With predefined distances from one another and from the shielding areas, electrical properties in respect of wave resistance and interfering incoming radiation can be achieved that are comparable to coaxial cables, or in the case of two parallel conductor paths, comparable to shielded symmetrical lines. Symmetrical lines are advantageous here, since, for example, the antenna loops themselves provide symmetrical signals. It is also conceivable here for there to be no carrier material, but another dielectric, including air, between two layers of the flexible carrier material 81 in the intermediate space of the two conductor paths in the plane.

Different combinations and functions can be realized by the basic options for the design of a flexible conductor segment 52 represented in FIG. 4. It would, for example, be conceivable for the conductor paths 82 on the surface to form part of a conductor loop 51 of an antenna. Provision could also be made here for conductor paths 82 electrically connected to one another on opposing surfaces of the conductor segment, which because of the skin effect can replace a separate, thick conductor. Shielded control and signal lines can be formed in the interior, which also combine conductor loops 51 with one another to form a matrix or connect them to a connection unit 70 for connection to the magnetic resonance tomography scanner 1. Supply voltages or currents can also be conducted to the function groups in this way.

The flexible conductor segment 52 can however also provide further electrical functions. Capacitances, which for example replace soldered-on extension capacitances, can be provided by opposing conductor surfaces comparable to the shielding areas 83, but without a conductor path 81 therebetween, only separated by a dielectric and electrically insulated from one another.

In regions in which a flexible conductor segment 52 is embodied by population simultaneously as an electronic function group, one or more of the layers of the flexible carrier material 81 can be embodied as bracing thanks to a greater thickness and/or additional layers made of the same carrier material or else a stiffer material can fulfill this purpose, in order to protect the attached components from mechanical stresses caused by bending and twisting.

By rolling up a flexible conductor segment 52 to form a drum or coil, the inductance of the conductor paths 81 in the flexible conductor segment 52 can also be increased or controlled. It is further conceivable for the flexible conductor segment to be guided through a sleeve balun or wound around a core. As a result and also in conjunction with the capacitances, standing wave traps can also be provided which prevent standing waves in particular on connections between the conductor loops.

Although the invention has been illustrated and described in greater detail with the preferred exemplary embodiment, the invention is not restricted by the examples disclosed and other variations can be derived therefrom by the person skilled in the art without departing from the protective scope of the invention. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

The invention claimed is:

1. A local coil for a magnetic resonance tomography scanner, the local coil comprising:
   an antenna having a conductor loop comprising a plurality of electronic function groups comprising at least a balun, a first preamplifier, and a matching network, wherein the balun and the matching network are each located adjacent to the first preamplifier along the conductor loop;
   wherein the electronic function groups are arranged in a distributed manner spaced apart from one another along the conductor loop and are electrically connected to one another by flexible conductor segments;
   wherein the flexible conductor segments include a flexible circuit board with at least three layers.

2. The local coil as claimed in claim 1, wherein components of a first one of the electronic function groups are arranged directly on a first one of the flexible conductor segments.

3. The local coil as claimed in claim 2, wherein the first flexible conductor segment has a bracing in a region of the first electronic function group.

4. The local coil as claimed in claim 3, wherein the bracing comprises a stiffer carrier material in the first flexible conductor segment and/or additional layers of a carrier material and/or a layer of the carrier material thicker in comparison to an adjacent flexible region.

5. The local coil as claimed in claim 1, wherein a first one of the flexible conductor segments has a shielded electrical signal line and/or a control line for the electronic function groups.

6. The local coil as claimed in claim 1, wherein a first one of the flexible conductor segments has a standing wave trap, wherein the first flexible conductor segment is rolled up to form a drum in the standing wave trap.

7. The local coil as claimed in claim 1, wherein the local coil has a plurality of antennas with a plurality of conductor loops and the plurality of antennas has electrically conductive connections on the conductor loops, with which the antennas are electrically connected to one another.

8. The local coil as claimed in claim 1, wherein one of the flexible conductor segments and one of the electronic function groups are electrically conductively connected to one another by a form-fit and/or force-fit connection.

9. The local coil as claimed in claim 1, wherein components of a first one of the electronic function groups are arranged directly on a first one of the flexible conductor segments.

10. The local coil as claimed in claim 9, wherein the first flexible conductor segment has a bracing in a region of the first electronic function group.

11. The local coil as claimed in claim 10, wherein the bracing comprises a stiffer carrier material in the first flexible conductor segment and/or additional layers of a carrier material and/or a layer of the carrier material thicker in comparison to an adjacent flexible region.

12. The local coil as claimed in claim 11, wherein the local coil has a plurality of antennas with a plurality of conductor loops and the plurality of antennas has electrically conductive connections on the conductor loops, with which the antennas are electrically connected to one another.

13. A local coil for a magnetic resonance tomography scanner, the local coil comprising:
   an antenna having a conductor loop comprising a plurality of electronic function groups comprising one or more of preamplifiers, baluns, mixers, diplexers, impedance matching networks, or safety circuits for protection of the antenna, patient, or antenna and patient;
   wherein the electronic function groups are arranged in a distributed manner spaced apart from one another along the conductor loop and are electrically connected to one another by flexible conductor segments;
   wherein components of a first electronic function group of the electronic function groups are arranged directly on a first flexible conductor segment of the flexible conductor segments, wherein the first flexible conductor segment includes a bracing in a region of the first electronic function group.

14. A local coil for a magnetic resonance tomography scanner, the local coil comprising:
   an antenna having a conductor loop comprising a plurality of electronic function groups comprising one or more of preamplifiers, baluns, mixers, diplexers, impedance matching networks, or safety circuits for protection of the antenna, patient, or antenna and patient;
   wherein the electronic function groups are arranged in a distributed manner spaced apart from one another along the conductor loop and are electrically connected to one another by flexible conductor segments; and
   wherein at least one of the flexible conductor segments has a standing wave trap, wherein the first flexible conductor segment is rolled up to form a drum in the standing wave trap.

15. The local coil of claim 1, wherein the electronic function groups further comprise at least a second preamplifier, a mixer, and a diplexer, wherein the mixer and diplexer are each located adjacent the second preamplifier along the extent of the conductor loop.

16. A local coil for a magnetic resonance tomography scanner, the local coil comprising:
   an antenna having a conductor loop comprising a plurality of electronic function groups comprising at least a balun, a first preamplifier, and a matching network, wherein the balun and the matching network are each located adjacent to the first preamplifier along the conductor loop;
   wherein the electronic function groups are arranged in a distributed manner spaced apart from one another along the conductor loop and are electrically connected to one another by flexible conductor segments;
   wherein at least one of the flexible conductor segments and at least one of the electronic function groups are electrically conductively connected to one another by a form-fit and/or force-fit connection.

* * * * *